(12) United States Patent
Fournier et al.

(10) Patent No.: US 10,993,623 B2
(45) Date of Patent: May 4, 2021

(54) DEVICE FOR CARRYING OUT MIRROR THERAPY, AND CORRESPONDING METHOD

(71) Applicant: Dessintey, St Jean Bonnefonds (FR)

(72) Inventors: Nicolas Fournier, St Victor sur Loire (FR); Davy Christophe Luneau, St Chamond (FR)

(73) Assignee: Dessintey

( * ) Notice: Subject to any disclaimer, the term of this patent is extended or adjusted under 35 U.S.C. 154(b) by 0 days.

(21) Appl. No.: 16/648,557

(22) PCT Filed: Sep. 10, 2018

(86) PCT No.: PCT/FR2018/052209
§ 371 (c)(1),
(2) Date: Mar. 18, 2020

(87) PCT Pub. No.: WO2019/068978
PCT Pub. Date: Apr. 11, 2019

(65) Prior Publication Data
US 2020/0214572 A1    Jul. 9, 2020

(30) Foreign Application Priority Data

Oct. 4, 2017 (FR) ...................................... 1759282

(51) Int. Cl.
*A61B 5/00*    (2006.01)
*G16H 40/63*    (2018.01)
(Continued)

(52) U.S. Cl.
CPC .......... *A61B 5/0079* (2013.01); *A61B 5/0036* (2018.08); *A61G 13/1235* (2013.01);
(Continued)

(58) Field of Classification Search
CPC .............. A61B 5/0079; A61B 5/00036; H04N 5/2253; H04N 7/183; H04N 5/44504;
(Continued)

(56) References Cited

U.S. PATENT DOCUMENTS

2008/0306572 A1   12/2008   Osada et al.
2011/0054870 A1*   3/2011   Dariush ................. G16H 50/50
                                                703/11
(Continued)

FOREIGN PATENT DOCUMENTS

| CN | 204016761 | 12/2014 |
|---|---|---|
| GB | 2436150 | 9/2007 |
| RO | 130153 | 4/2015 |

OTHER PUBLICATIONS

Lee, Hsin-Min, et al, "Delayed Mirror Visual Feedback Presented Using a Novel Mirror Therapy System Enhances Cortical Activation in Healthy Adults"; Journal of NeuroEngineering and Rehabilitation (2015) 12:56.

*Primary Examiner* — Navin Natnithithadha
*Assistant Examiner* — Sunita Reddy
(74) *Attorney, Agent, or Firm* — Forge IP, PLLC

(57) ABSTRACT

A device for carrying out mirror therapy includes: a camera for filming a healthy limb of a patient, a work surface on which the patient positions his healthy limb or affected limb, a screen for displaying the image of the healthy limb which is positioned on the work surface and which is filmed by the camera, the screen preventing the patient from directly seeing his healthy limb or affected limb on the work surface, and a support structure which is connected to the work surface and on which the screen and the camera are mounted. The device has a mirror fixed behind the screen. The camera films the healthy limb reflected in the mirror, and the image displayed by the screen is a reflection of the healthy limb in the mirror.

10 Claims, 4 Drawing Sheets

(51) Int. Cl.
| | |
|---|---|
| *G16H 20/70* | (2018.01) |
| *A61G 13/12* | (2006.01) |
| *G09B 5/02* | (2006.01) |
| *A61M 21/00* | (2006.01) |
| *H04N 5/225* | (2006.01) |
| *H04N 7/18* | (2006.01) |
| *H04N 5/445* | (2011.01) |

(52) U.S. Cl.
CPC ............... *A61M 21/00* (2013.01); *G09B 5/02* (2013.01); *G16H 20/70* (2018.01); *G16H 40/63* (2018.01); *H04N 5/2253* (2013.01); *H04N 5/44504* (2013.01); *H04N 7/183* (2013.01); *A61M 2021/005* (2013.01)

(58) Field of Classification Search
CPC ... G09B 5/02; A61F 2002/5058; G16H 40/63; G16H 20/30; G16H 20/70; A63B 2225/12; A61M 2021/005; A61M 21/00; A61G 13/1235
USPC .................................................. 128/897–899
See application file for complete search history.

(56) References Cited

U.S. PATENT DOCUMENTS

| | | | |
|---|---|---|---|
| 2012/0206577 A1* | 8/2012 | Guckenberger | G09B 19/003 348/47 |
| 2015/0313793 A1 | 11/2015 | Lee et al. | |
| 2016/0249008 A1* | 8/2016 | Kitazawa | G06F 19/3481 |
| 2017/0113015 A1* | 4/2017 | Kaneko | A61N 1/0456 |
| 2017/0365101 A1* | 12/2017 | Samec | G02B 27/017 |
| 2018/0082600 A1* | 3/2018 | Ortiz Catalan | G06F 3/017 |
| 2018/0121728 A1* | 5/2018 | Wells | G06T 19/006 |

* cited by examiner

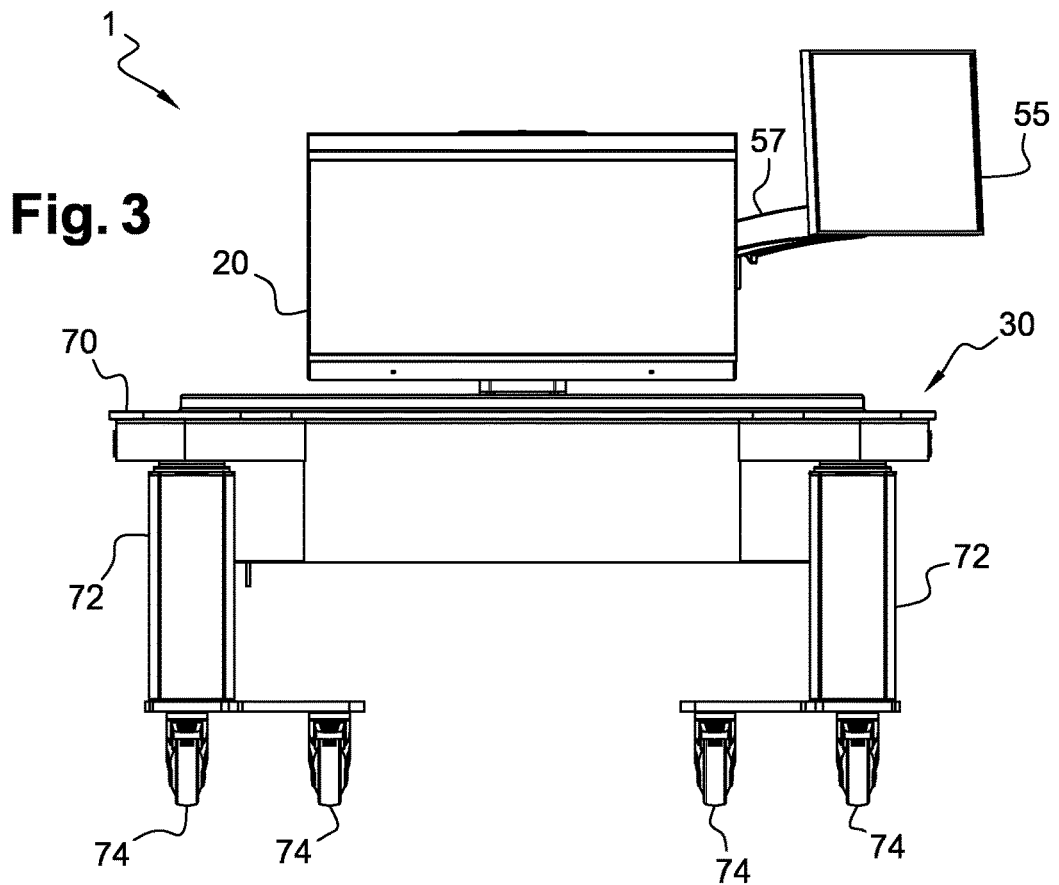
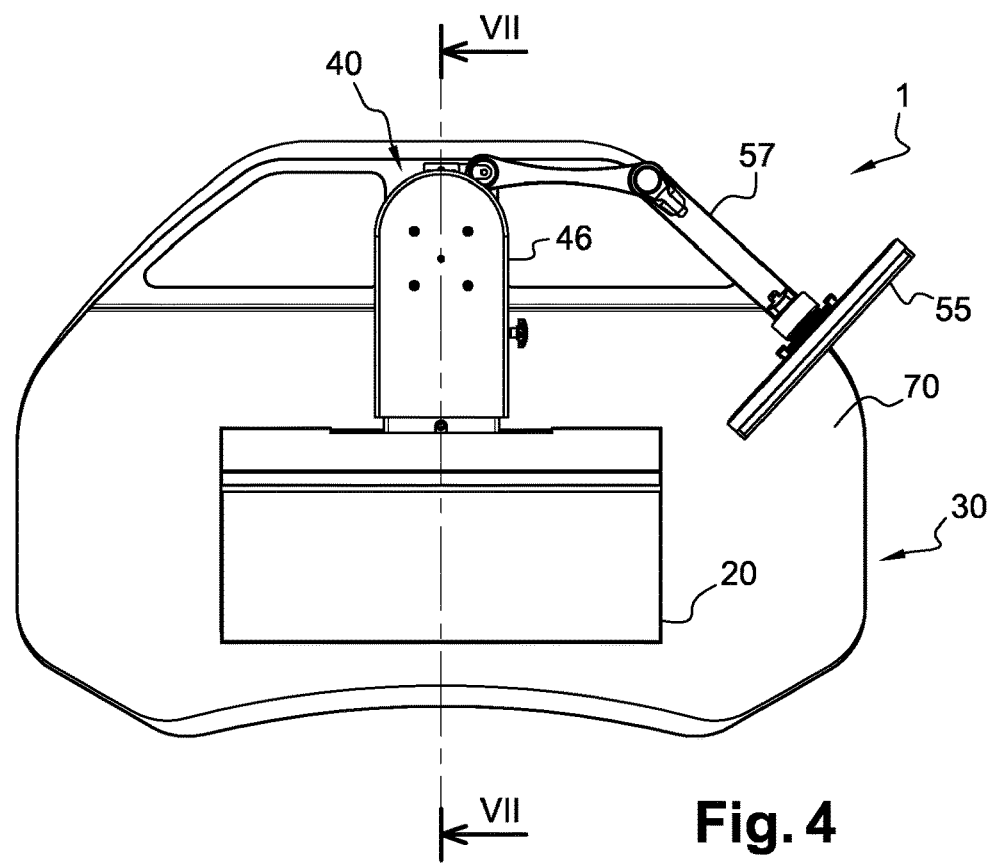

DEVICE FOR CARRYING OUT MIRROR THERAPY, AND CORRESPONDING METHOD

TECHNICAL FIELD

This invention relates to the technical field of equipment for neuromotor reeducation and rehabilitation.

PRIOR ART

Devices for neuromotor reeducation and rehabilitation, for implementing mirror therapy, are known from the state of the art. Mirror therapy consists in making the brain believe that a deficient limb is healthy by an optical illusion system.

Conventionally, a mirror may be used so that, when a patient looks at a reflection of a healthy limb in this mirror, the patient has the impression of moving a deficient limb. Thus, by virtue of the brain's plasticity, remodeling of neural connections is possible, with advantageous results for overcoming chronic pain or a motor deficiency of the limb. An example of a device for mirror therapy is disclosed in patent GB 2 436 150.

More recently, electronic devices have been developed for mirror therapy. These devices comprise a camera, a screen and a support system, to ensure a good relative position between the various elements of the device and the patient. Thus, the reflection of a limb is replaced by a digitally modified image. Such devices are disclosed for example in patent applications RO 130153, US 2015 313793 and CN 204016761.

An electronic device generally has the disadvantage of requiring a significant adjustment time before use. Indeed, the device must be adjusted based on the morphology of each patient, especially his/her build, deportment, posture and movement possibilities, which are influenced by his/her deficiencies or disability. Due to the significant amount of time setting up the patient at each session, the effectiveness of the treatment is reduced.

Moreover, the quality of the illusion is often mediocre: it does not reproduce the eye-hand vision identically to what the patient would see without the device. The efficacy of the illusion is adversely affected.

BRIEF DESCRIPTION OF THE INVENTION

One of the aims of the invention is therefore to propose a device which will be simple to implement, with easy adjustability. It should be noted that the work zone must always be correctly chosen to generate a plausible image, which is essential for obtaining an illusion effect which forms the basis of the therapy.

By way of example, a hemiplegic person often suffers muscular contractions of his upper limbs, and therefore has difficulties positioning his arm on the work bench. There is thus a need to move the screen toward them while filming the correct work zone.

In practice, the technique consists in filming the healthy limb which is not suffering from contractions. It is necessary to be able to correctly film the healthy arm of the patient placed on the bench, then to invert the video, and to play this video over the affected arm of the patient having retractions. For this playing phase, it is essential that the patient is settled comfortably and that a perfect illusion can be provided: i.e. that the illusion on the screen has perfect continuity with his affected arm, in order that they are convinced that his affected arm is moving normally.

Another aim of the invention is to provide a simple and compact device. It is also important to ensure good overall stability.

In order to solve the above-mentioned problems, a device has been developed for carrying out mirror therapy, comprising:
- a camera for filming a healthy limb of a patient,
- a work surface on which the patient positions his healthy limb or affected limb,
- a screen capable of displaying the image of the healthy limb, which is positioned on the work surface, and which is filmed by the camera, said screen preventing the patient from directly seeing his healthy limb or affected limb on the work surface, and
- a support structure which is connected to the work surface and on which the screen and the camera are mounted.

According to the invention, the device comprises a mirror fixed behind the screen, and the camera films the healthy limb reflected in the mirror. The image displayed by the screen is a reflection of the healthy limb in the mirror.

In this way, the device facilitates the adjustment necessary for carrying out the mirror therapy. The use of the camera filming the healthy limb not directly, but via the mirror, allows to adapt the device more easily to the needs of each patient.

The work surface is designed to comfortably accommodate the healthy limb in a first phase of recording, then the affected limb in a second phase of playing.

During this phase of playing, the image of the healthy limb displayed on the screen is superimposed on the affected limb of the patient positioned on the work surface. The patient can then perform exercises for reeducation of the affected limb.

According to a particularly advantageous feature, the camera, the screen, the mirror and a part of the support structure are mobile relative to the work surface, forming a monolithic system.

Thereby, the device is simpler, and the adjustments required for implementation thereof are minimized, while providing a large degree of adaptation flexibility.

Preferably, the support structure is horizontally adjustable relative to the work surface, by being brought closer to or moved away from the patient.

Still preferably, the support structure is adjustable in height relative to the work surface, to facilitate the setting-up of the affected limb of the patient (in particular if this limb has to be held by a splint or a foam support).

According to an advantageous embodiment, a constant distance is defined between the camera and the mirror. Preferably, the mirror is fixed parallel to the screen. The adjustment is thus further facilitated. It is sufficient to move the support structure for the distance between the patient's eyes to be equal to the distance between the camera and the mirror.

Further preferably, an angle, defined between the work surface and a plane coplanar to the screen, in a plane perpendicular to the work surface and to the mirror, has a fixed value. Even more advantageously, this angle is equal to 53°.

Advantageously, the device comprises a screen for managing/controlling a work session, accessible to a practitioner.

The invention also relates to a method for implementing the device, as described hereinbefore.

According to the invention, the method comprises the following steps:
  a) the patient positions his healthy limb on the work surface;
  b) the healthy limb is reflected in the mirror;
  c) the support structure is adjusted so that a total optical path between the eye of the patient and his healthy limb and the optical path between the camera and the healthy limb of the patient are identical;
  d) the camera films the reflection in the mirror of the healthy limb;
  e) the patient positions his affected limb on the work surface;
  f) the screen displays the image of the healthy limb filmed by the camera;
  g) the support structure is adjusted so that the image of the healthy limb displayed on the screen is superimposed on the affected limb of the patient positioned on the work surface.

Steps a), b), c) and d) constitute the first phase of recording, while steps e), f) and g) constitute the second phase of playing.

BRIEF DESCRIPTION OF THE DRAWINGS

Further characteristics and advantages of the invention will become apparent from the description provided below, which is for reference only and is in no way restrictive, with reference to the accompanying figures, in which:

FIG. 3 is a front view of the device;

FIG. 4 is a top view of the device;

For the sake of clarity, the same elements bear the same numerical references on the different figures.

DETAILED DESCRIPTION OF THE INVENTION

This invention relates to a device (1) for carrying out mirror therapy.

Figure 1:
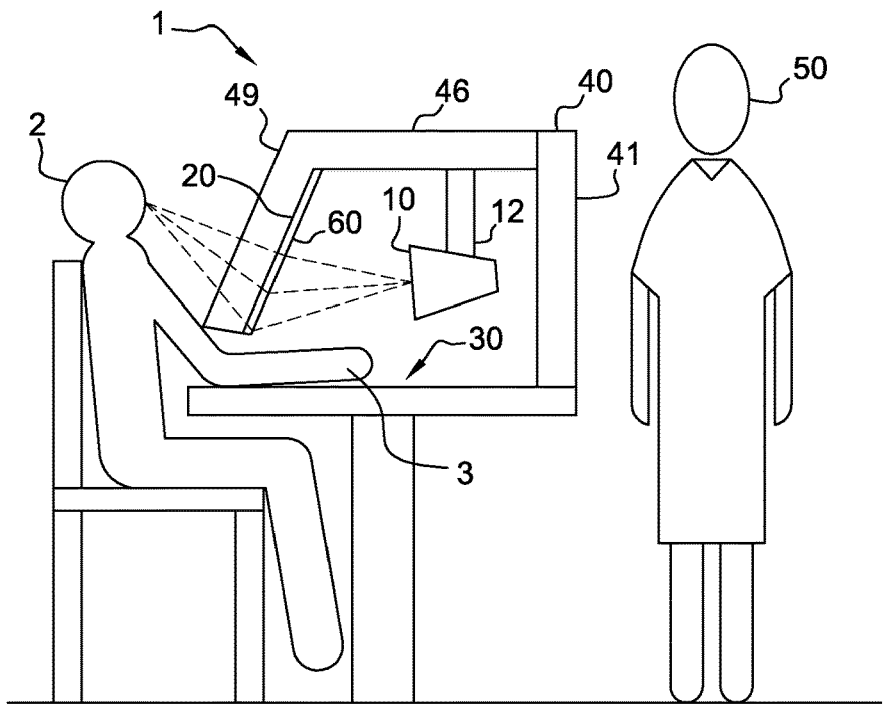
FIG. 1 is a schematic depiction of the device according to the invention, showing the principle of the invention.
Figure 2:
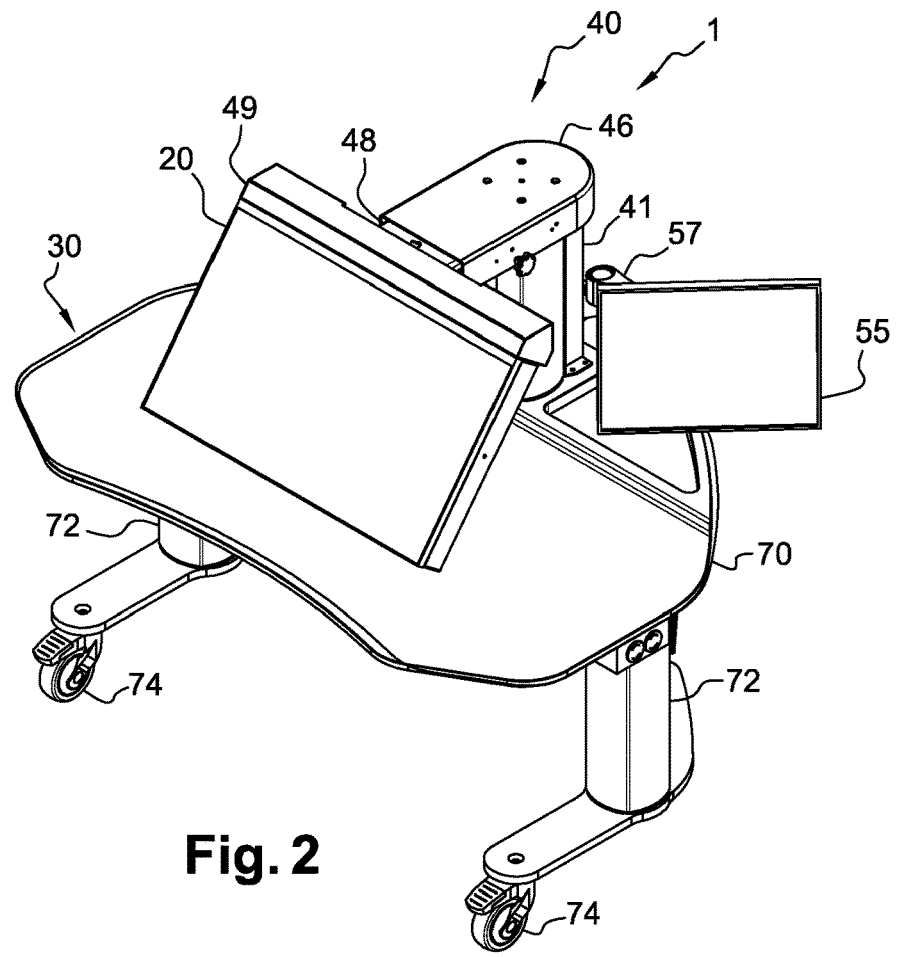
FIG. 2 is a schematic isometric depiction of the device.
Figure 5:
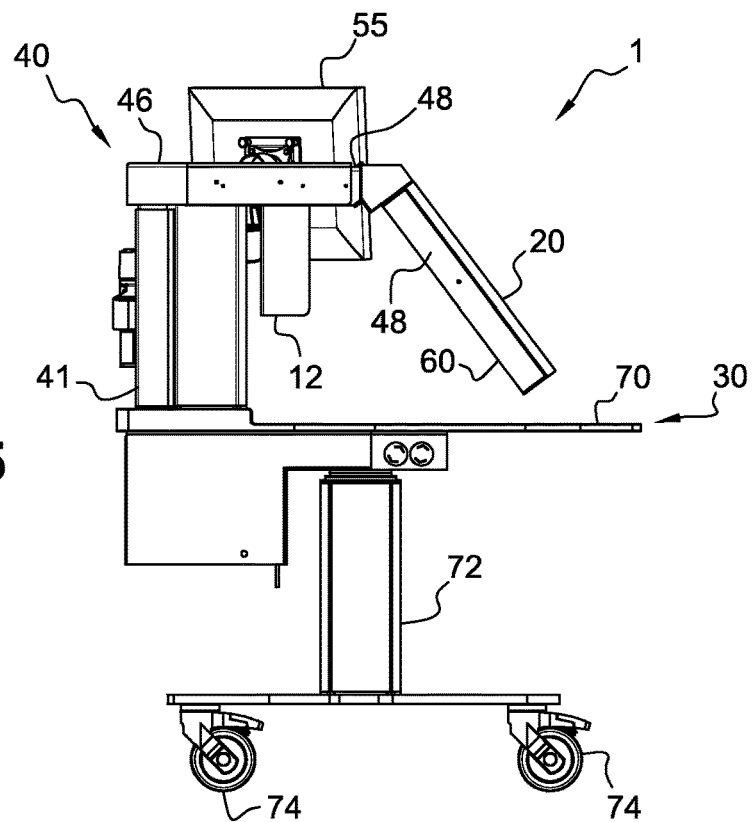
FIG. 5 is a side view of the device.
Figure 6:
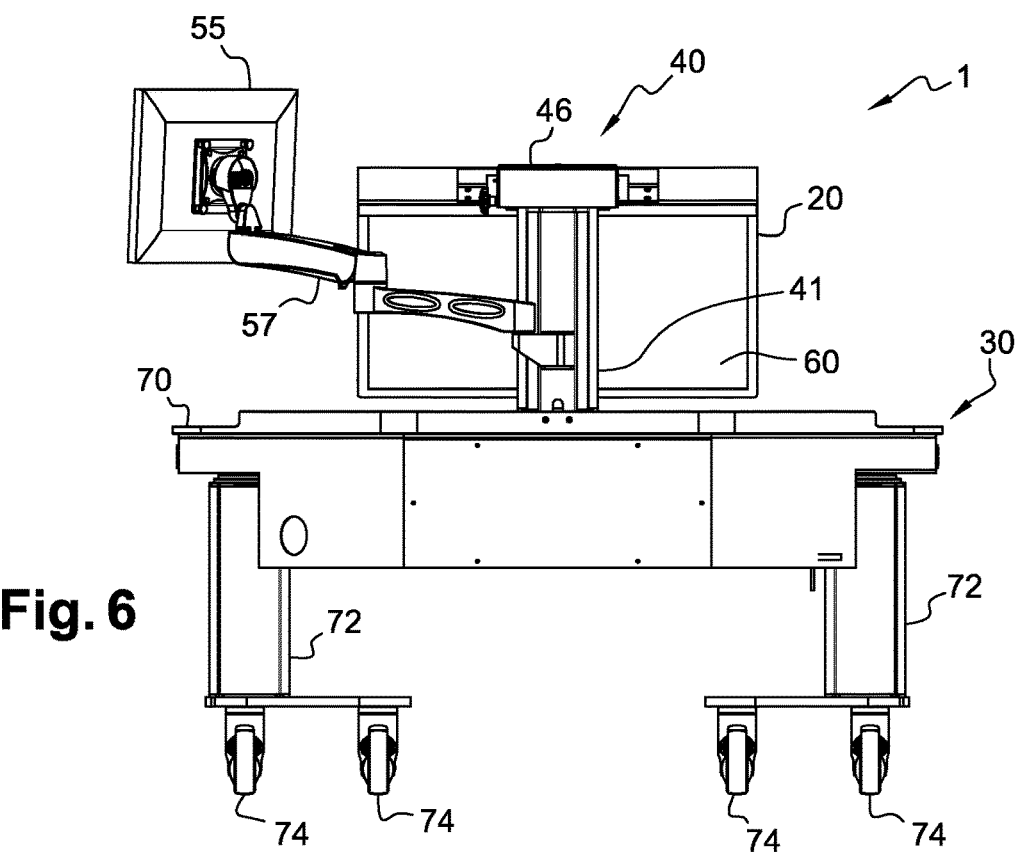
FIG. 6 is a rear view of the device.
Figure 7:
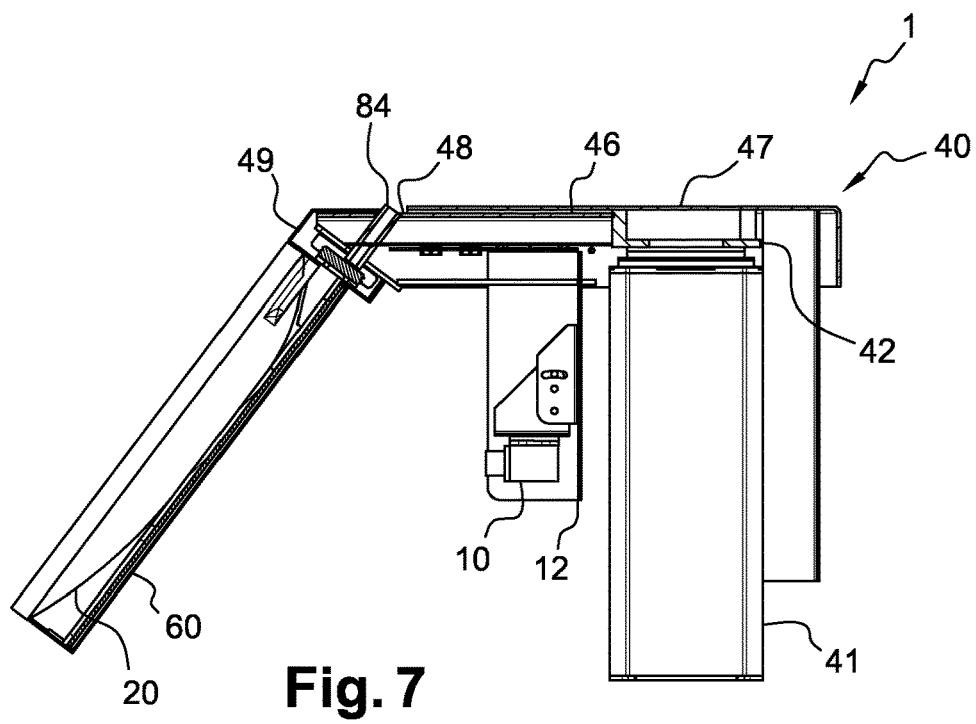
FIG. 7 is a sectional view of the device, along the line VII-VII from FIG. 4.
Figure 8:
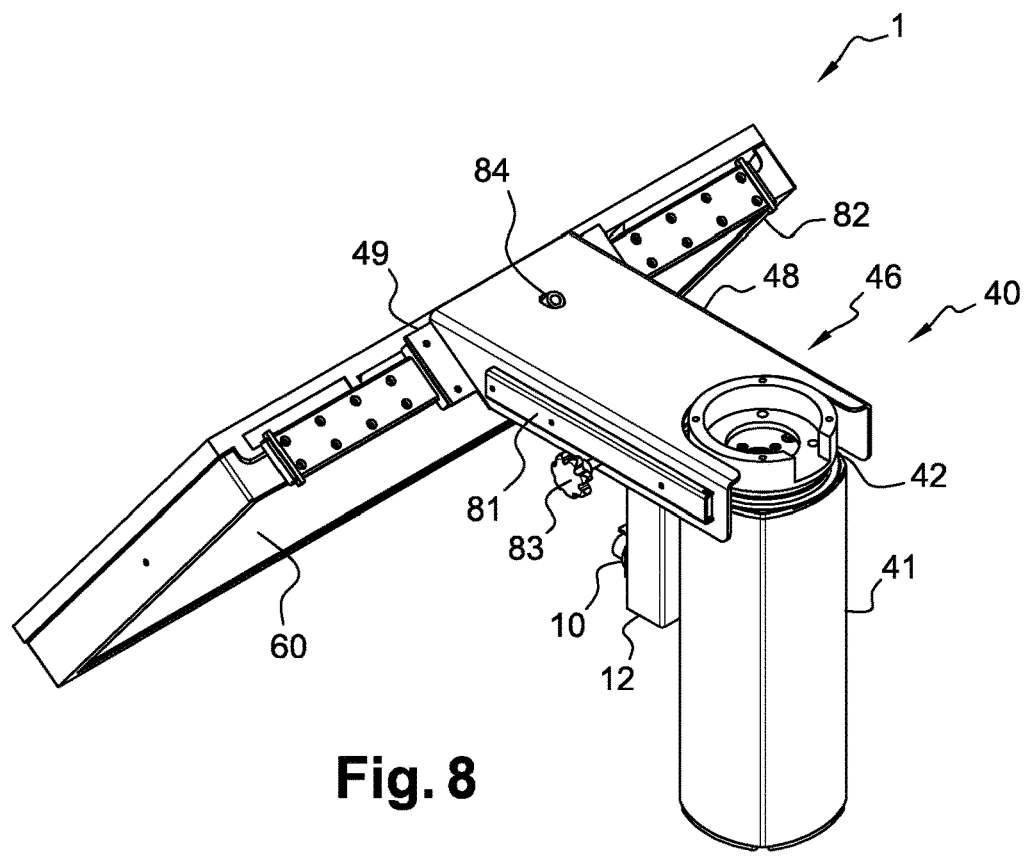
FIG. 8 is a perspective view of the device, showing the adjustment elements.

FIG. 1 illustrates the principle of the device (1). In a manner known to a person skilled in the art, mirror therapy consists in showing the patient (2) a false image of his/her deficient limb. In the case in point, the patient (2) sees a transformed image of his/her healthy limb (3). Consequently, the brain believes that the deficient limb is performing sequences of movements which are actually being performed by the healthy limb (3).

By virtue of the brain's plasticity, remodeling of neural connections is possible and allows to obtain advantageous results for overcoming chronic pain or a motor deficiency of the limb. The aforementioned image transformation may be a reflection in a mirror, hence the name of the therapy.

However, the use of a mirror requires the patient (2) to maintain a relatively uncomfortable position to correctly see the reflection, which greatly limits the duration of the therapeutic sessions.

In the disclosure below, "limb" denotes the arm and/or the hand of the patient (2). Alternatively, the "limb" may be the leg and/or the foot of the patient (2).

Conventionally, an electronic device for mirror therapy comprises a camera (10) and a screen (20). The device comprises a processor executing an algorithm, which allows to transform a filmed image by performing a symmetrical reflection and a distortion correction. However, implementing the device requires meticulous adjustment for each patient (2), in order to obtain a good image, which still limits the time available for the therapy per se.

It is necessary to meet both of the following conditions for the viewing to be plausible:
  The total optical path between the eye of the patient (2) and his healthy limb (3) and the optical path between the camera (10) and the healthy limb (3) of the patient (2) must be identical.
  The angle formed by the sight line extending from the eyes of the patient (2) to his limb, said angle being measured relative to the work surface (30), must be the same as the angle formed by the sight line extending from the camera (10) to the mirror (60) measured relative to the plane normal to the mirror (60).

In summary, the patient (2) sees his limb through the screen (20) with the same perspective as if they were looking directly at it.

To meet these demands safely, simply and effectively, a device (1) in accordance with the invention is proposed. The device (1) comprises, in a known manner:
  a camera (10) for filming a healthy limb (3) of a patient (2);
  a work surface (30) on which the patient (2) positions his healthy limb (3) and/or his affected limb;
  a screen (20) capable of displaying the image of the healthy limb (3), which is positioned on the work surface (30), and which is filmed by the camera (10). The screen (20) prevents the patient (2) from directly seeing his healthy or deficient limb on the work surface.

The device (1) also comprises a support structure (40) which is connected to the work surface (30), and on which the screen (20) and the camera (10) are mounted. The support structure (40) will be detailed hereafter.

The device (1) is suitable for use by the patient (2) autonomously or under the supervision of a practitioner (50), who may be a doctor, physical therapist or another health care professional. Autonomous operation is in particular made possible by software comprising descriptions of exercises. The practitioner (50) has another dedicated software, enabling them in addition to evaluate the efficacy of the therapy, and to plan the treatment.

According to the invention, a mirror (60) is fixed behind the screen (20). The camera (10) films the healthy limb (3) reflected in the mirror (60). In other words, the image displayed by the screen (20) is a reflection of the limb (3) in said mirror (60). The mirror (60) is fixed parallel to the screen (20), to ensure equality of the angles already mentioned.

Referring to FIGS. 2 to 8, the construction details of the device (1) will now be described.

The work surface (30) is preferably a table (70). The table (70) is installed on height-adjustable legs (72) with casters (74) at the ends thereof to facilitate moving and storing the device (1). The work surface (30) is filmed by the camera (10). According to the experiments which led to the design of the device (1), the optimal size of the work surface (30) is approximately 800 mm wide in the right-left direction for the patient (2) using the device (1), and 450 mm long in the direction of the axis between the patient (2) and the camera (10).

The present disclosure relates more particularly to a device (1) adapted to therapy of the upper limbs. Of course, the device (1) may just as well be used for mirror therapy of a lower limb. In this case, the work surface (30) is arranged lower, and the size thereof is accordingly adapted. In this embodiment variant, the principle of the invention remains the same, so that the structural differences will not be described in detail.

The support structure (40) comprises two parts. A fixed part (41) is securely attached to the table (70). A mobile part (46) is articulated relative to the fixed part (41). The camera (10), the screen (20), the mirror (60) and the mobile part (46) form a monolithic system. The mobile part (46) comprises two horizontal elements, a guide (47) and a slider (48), and an inclined element (49). The camera (10) is arranged in a support (12) for camera (10), which is securely attached to the slider (48) of the mobile part (46). The screen (20) and the mirror (60) are securely attached to the inclined element (49) of the mobile part (46).

The support structure (40) is horizontally adjustable relative to the work surface (30), the mobile part (46) being brought closer to or moved further away from the patient (2). This adjustment is possible for example by virtue of a slide rail (81), enabling translation between the guide (47) and the slider (48) of the mobile part (46).

Advantageously, the screen (20) is also laterally adjustable. This adjustment is possible for example by virtue of a slide rail (82), enabling translation between the screen (20), securely attached to the inclined element (49), and the slider (48).

The support structure (40) is also adjustable in terms of height relative to the work surface (30). To this end, the fixed part (41) incorporates a telescopic foot (42) allowing to modify the height of the mobile part (46) relative to said table (30). The foot (42) is fixed to the guide (47), for example by screws.

The therapist (50) may choose to raise or lower the mobile part (46) and therefore the screen (20) based on the patient (2) (in order to position the patient (2) comfortably, in particular his affected arm with splint or support, for example).

In other words, the guide (47) of the mobile part (46) is movable in terms of height relative to the work surface (30). As a result, the slider (48) is also movable in terms of height, and in addition is mobile in translation in a horizontal direction relative to the guide (47). Finally, the inclined element (49) is mobile in a vertical direction and in two horizontal directions.

It is important to mention that the lateral adjustment of the screen (20) along the axis of the slide rail (82) allows it to position the image of a limb on the screen (20) in continuity with the affected limb of the patient (2), and this in order to promote the illusion. The patient (2) thus believes that it is his real limb on the screen (20).

The slide rails (81) and (82) have adjuster dials, (83) and (84) respectively, to block the position of the slider (47) and of the element (48) once they have been adjusted.

In order to use the invention, the patient (2) sits on a chair in front of the device (1).

A session takes place in two phases: a first phase of recording and a second phase of playing.

The first phase comprises the following steps:

The patient (2) places his healthy limb (3) on the work surface (30).

Adjustments are made to ensure a comfortable position for the patient (2) and to enable the camera (10) to correctly record a reflection of the healthy limb (3).

A video of movements performed by the healthy limb (3) is recorded.

Several movements may be performed, and each is recorded separately.

The patient (2) removes his healthy limb (3) from the work surface (30).

Next, the system inverts the videos so that, for example, a right limb is able to be displayed as a left limb.

The second phase comprises the following steps:

The patient (2) places his affected limb on the work surface (30).

Adjustments are made to ensure a comfortable position for the patient (2) and so that the limb on the screen (20) is displayed in continuity with the affected limb, i.e. by superimposing the modified image of the healthy limb (3) with the location of the affected limb.

The display of the inverted film is started on the screen (20).

To explain the adjustments of the first phase in more detail, the device (1) is considered to be correctly adjusted when the total optical path between the eye of the patient (2) and his healthy limb (3) is equal to the optical path between the camera (10) and the healthy limb (3) of the patient (2), i.e. the distance between the camera (10) and the mirror (60) plus the distance between the mirror (60) and the healthy limb (3) of the patient (2).

When the support structure (40) is adjusted, the healthy limb (3), reflected in the mirror (60), is filmed by the camera (10) with a geometric relationship identical to that with which the patient (2) looks at the image on the screen (20).

Advantageously, the practitioner (50) has a dedicated screen (55), installed on an arm (57) allowing it to easily change the position thereof. This screen (55) enables the practitioner (50) to manage/control the work session of the patient (2).

Thus, as emerges from the foregoing disclosure, the device (1) according to the invention is easy to implement, in particular with convenient adjustability. It should be noted that the work zone is always well-suited to generate a plausible image in order to obtain an illusion effect necessary for carrying out the therapy.

The invention claimed is:

1. A device for carrying out mirror therapy, comprising:
a camera configured for filming a healthy limb of a patient,
a work surface configured for positioning the healthy limb or an affected limb of the patient on the work surface,
a screen configured for displaying an image of the healthy limb positioned on the work surface, the healthy limb being filmed by the camera, said screen preventing the patient from directly seeing the healthy limb or the affected limb on the work surface, and
a support structure which is connected to the work surface, the screen and the camera being mounted on said support structure,
wherein the device comprises a mirror fixed behind the screen, wherein the camera films the healthy limb reflected in the mirror, and wherein the image displayed by the screen is a reflection of the healthy limb in said mirror.

2. The device according to claim 1, wherein the camera, the screen, the mirror and a part of the support structure mobile relative to the work surface together form a monolithic system.

3. The device according to claim 1, wherein the support structure is horizontally adjustable relative to the work surface, by being brought closer to or moved away from the patient.

4. The device according to claim 1, wherein the support structure is adjustable in height relative to the work surface.

5. The device according to claim 1, wherein a constant distance is defined between the camera and the mirror.

6. The device according to claim 1, wherein the mirror is fixed parallel to the screen.

7. The device according to claim 1, wherein an angle defined between the work surface and a plane coplanar to the screen, in a plane perpendicular to the work surface and to the mirror, has a fixed value.

8. The device according to claim 7, wherein the angle is equal to 53°.

9. The device according to claim 1, wherein the device comprises a screen for managing or controlling a work session, accessible to a practitioner.

10. A method of using the device according to claim 1, wherein the method comprises the following steps:
    a) the patient positions the healthy limb on the work surface;
    b) the healthy limb is reflected in the mirror, which creates a reflection of the healthy limb in said mirror;
    c) a total optical path between an eye of the patient and the healthy limb and the optical path between the camera and the healthy limb of the patient are made identical by adjusting the support structure;
    d) the camera films the reflection in the mirror of the healthy limb;
    e) the patient positions the affected limb on the work surface;
    f) the screen displays the image of the reflection of the healthy limb filmed by the camera;
    g) the image of the healthy limb displayed on the screen is superimposed on the affected limb of the patient positioned on the work surface by adjusting the support structure.

* * * * *